US009693745B2

(12) United States Patent
Teshigawara

(10) Patent No.: US 9,693,745 B2
(45) Date of Patent: Jul. 4, 2017

(54) X-RAY COMPUTED TOMOGRAPHY APPARATUS, X-RAY DETECTION APPARATUS, AND X-RAY DETECTION MODULE

(71) Applicant: Toshiba Medical Systems Corporation, Otawara-shi (JP)

(72) Inventor: Manabu Teshigawara, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 215 days.

(21) Appl. No.: 14/564,562

(22) Filed: Dec. 9, 2014

(65) Prior Publication Data

US 2015/0173694 A1 Jun. 25, 2015

Related U.S. Application Data

(63) Continuation of application No. PCT/JP2013/079012, filed on Oct. 25, 2013.

(30) Foreign Application Priority Data

Oct. 26, 2012 (JP) ................................ 2012-236555

(51) Int. Cl.
*A61B 6/06* (2006.01)
*A61B 6/03* (2006.01)
(Continued)

(52) U.S. Cl.
CPC .............. *A61B 6/4291* (2013.01); *A61B 6/06* (2013.01); *A61B 6/4233* (2013.01);
(Continued)

(58) Field of Classification Search
CPC .... A61B 6/00; A61B 6/03; A61B 6/06; A61B 6/42; A61B 6/4208; A61B 6/4233;
(Continued)

(56) References Cited

U.S. PATENT DOCUMENTS

2001/0033636 A1* 10/2001 Hartick .................. G01N 23/20
378/88
2003/0205675 A1* 11/2003 Nelson ................. A61B 6/4233
250/370.09
(Continued)

FOREIGN PATENT DOCUMENTS

CN 101218501 A 7/2008
CN 101680955 A 3/2010
(Continued)

OTHER PUBLICATIONS

Combined Chinese Office Action and Search Report issued Nov. 2, 2015 in Patent Application No. 201380002387.8 (with English Translation of Category of Cited Documents).
(Continued)

*Primary Examiner* — Anastasia Midkiff
(74) *Attorney, Agent, or Firm* — Oblon, McClelland, Maier & Neustadt, L.L.P.

(57) ABSTRACT

An X-ray computed tomography apparatus includes an X-ray generation circuit generating X-rays, X-ray detection circuit including X-ray detection modules detecting the X-rays for respective energy widths, counting circuit counting a photon originating from the X-rays for the respective energy widths based on an output from the X-ray detection circuit, and reconstruction circuit reconstructing a medical image based on an output from the counting circuit. Each of the X-ray detection modules includes a collimator collimating the X-rays, diffraction cell arranged on a rear surface side of the collimator and diffracting the X-ray at an angle corresponding to an energy of the X-ray, and X-ray detector cells arranged in a predetermined distance away from a rear surface of the collimator, and detecting the diffracted X-ray.

5 Claims, 6 Drawing Sheets

(51) Int. Cl.
*A61B 6/00* (2006.01)
*H04N 5/32* (2006.01)

(52) U.S. Cl.
CPC .......... *A61B 6/4266* (2013.01); *A61B 6/032* (2013.01); *A61B 6/4035* (2013.01); *A61B 6/4241* (2013.01); *A61B 6/482* (2013.01); *A61B 6/5205* (2013.01); *H04N 5/32* (2013.01)

(58) Field of Classification Search
CPC ....... A61B 6/4266; A61B 6/4291; A61B 6/48; A61B 6/485; A61B 6/483; A61B 2560/00; A61B 2560/04; A61B 2560/06; H01L 27/00; H01L 27/14; H01L 27/142; H01L 27/144; H01L 27/1446; H01L 27/146; H01L 27/14601; H01L 27/14609; H01L 27/14618; H01L 27/14625; H01L 27/14641; H01L 27/14643; H01L 27/14658; H01L 27/14659; H01L 27/14663; H01L 27/14665; H01L 27/14676; H01L 27/148; H01L 27/14806; H01L 27/14812; H01L 27/14818; H01L 27/14831; H01L 27/1485; H01L 27/14893; G01T 1/00; G01T 1/15; G01T 1/16; G01T 1/161; G01T 1/18; G01T 1/20; G01T 1/2002; G01T 1/2006; G01T 1/2018; G01T 1/24; G01T 1/243; G01T 1/244; G01T 1/247; G01T 1/249; G01T 1/29; G01T 1/36; G01T 1/362; G01T 1/366; G01T 7/00; G01N 23/00; G01N 23/02; G01N 23/04; G01N 23/046; G01N 23/06; G01N 23/08; G01N 23/083; G01N 23/087; G01N 23/20; G01N 23/20008; G01N 23/20091; G01N 2223/00; G01N 2223/03–2223/05; G01N 2223/056; G01N 2223/0563; G01N 2223/30; G01N 2223/316; G01N 2223/40; G01N 2223/413; G01N 2223/419; G01N 2223/423; G01N 2223/50; G01N 2223/501; G01N 2223/505; G01N 2223/5055; G21K 1/00; G21K 1/02; G21K 1/06; G21K 2201/00; G21K 2201/06; G21K 2201/062; G21K 2201/067; G02B 5/00; G02B 5/005; G02B 5/02; G02B 5/0273; G02B 5/0278; G02B 5/18; G02B 5/1838; G02B 5/1842; G02B 5/1866; G02B 6/00; G02B 6/0011; G02B 6/0033; G02B 6/005; G02B 6/0051; G02B 6/0096; G02B 27/0944; G02B 27/1086; G02B 27/30; G02B 27/42; G02B 27/4205; G02B 27/4277; G02B 27/4233; G02B 27/4244; G01R 23/02; G01R 23/10

See application file for complete search history.

(56) References Cited

U.S. PATENT DOCUMENTS

| | | | |
|---|---|---|---|
| 2004/0174959 A1* | 9/2004 | Green | G01N 23/20 378/146 |
| 2008/0226019 A1 | 9/2008 | Thran et al. | |
| 2009/0225945 A1* | 9/2009 | Smither | G01N 23/046 378/71 |
| 2009/0302232 A1* | 12/2009 | Grosholz, Jr. | G01T 1/17 250/394 |
| 2010/0187432 A1 | 7/2010 | Herrmann et al. | |
| 2013/0010927 A1* | 1/2013 | Seppi | A61B 6/032 378/86 |

FOREIGN PATENT DOCUMENTS

| | | |
|---|---|---|
| JP | 61-240146 A | 10/1986 |
| JP | 7-21469 B2 | 3/1995 |
| JP | 2010-530535 | 9/2010 |

OTHER PUBLICATIONS

English translation of the International Preliminary Report on Patentability and Written Opinion issued May 7, 2015 in PCT/JP2013/079012.

International Search Report issued Nov. 26, 2013 for PCT/JP2013/079012 filed on Oct. 25, 2013 (with English translation).

International Written Opinion mailed on Nov. 26, 2013 for PCT/JP2013/079012 filed on Oct. 25, 2013.

Combined Office Action and Search Report issued Jun. 29, 2016 in Chinese Patent Application No. 201380002387.8 (with English translation of Categories of Cited Documents).

\* cited by examiner

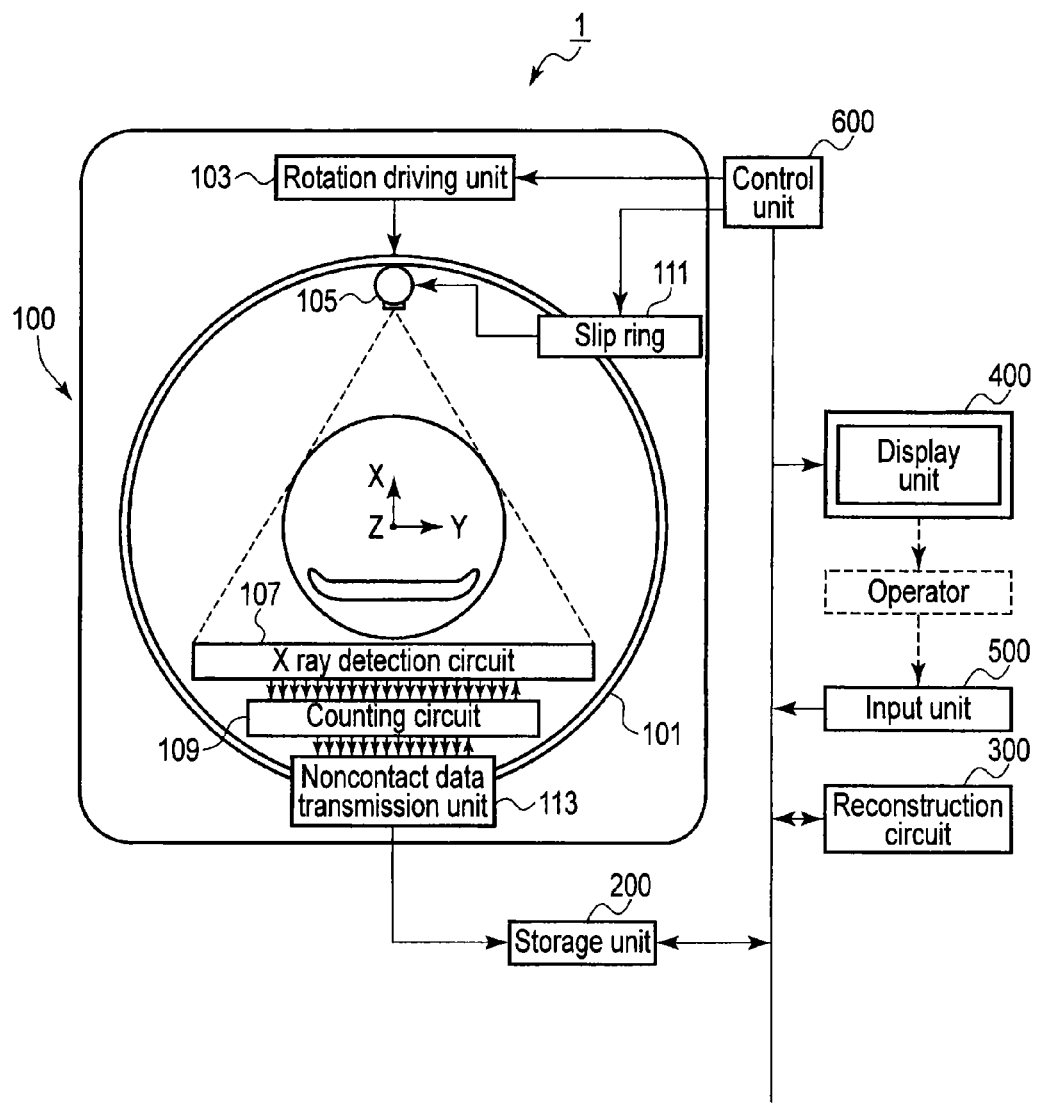
F I G. 1

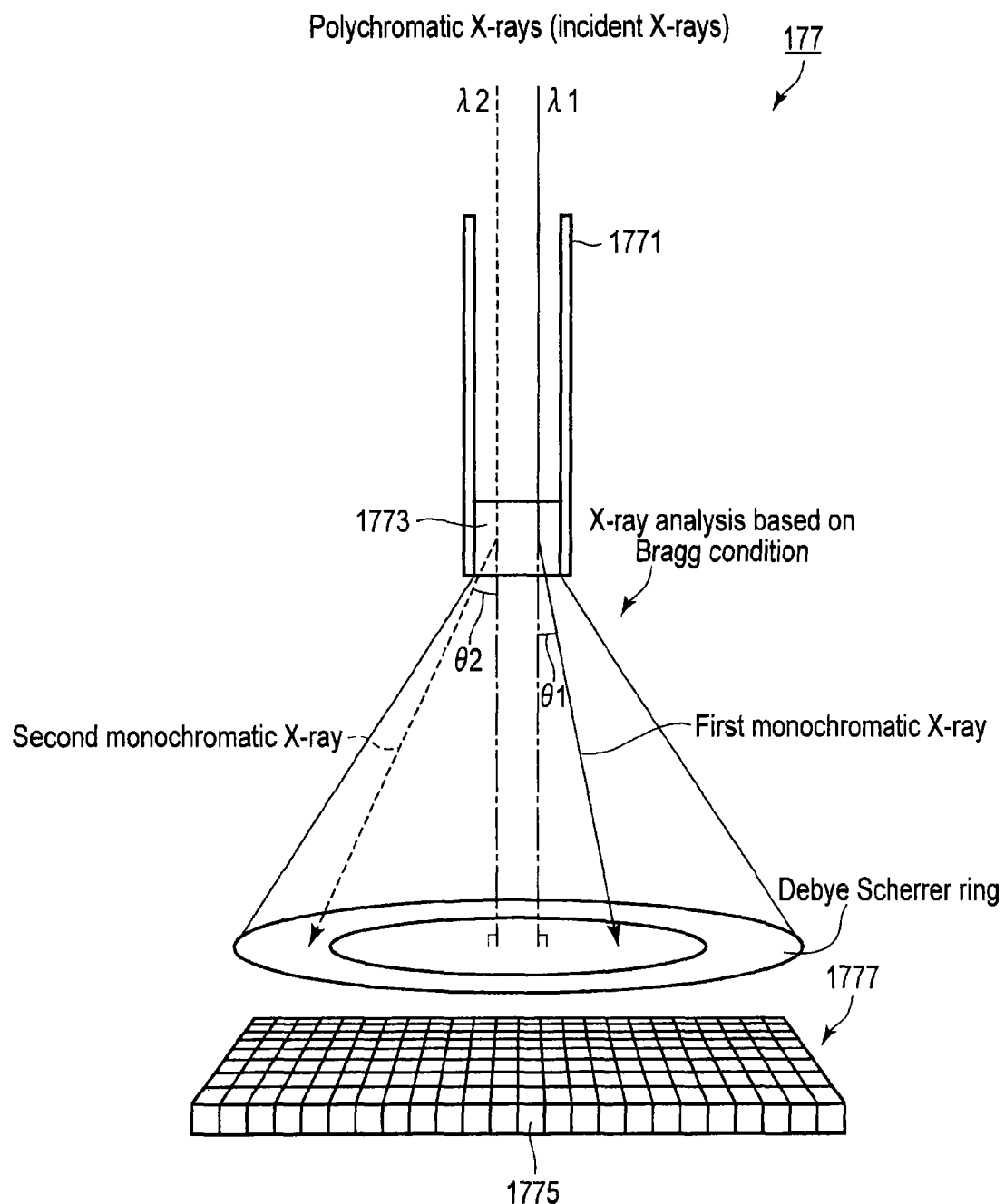
F I G. 3

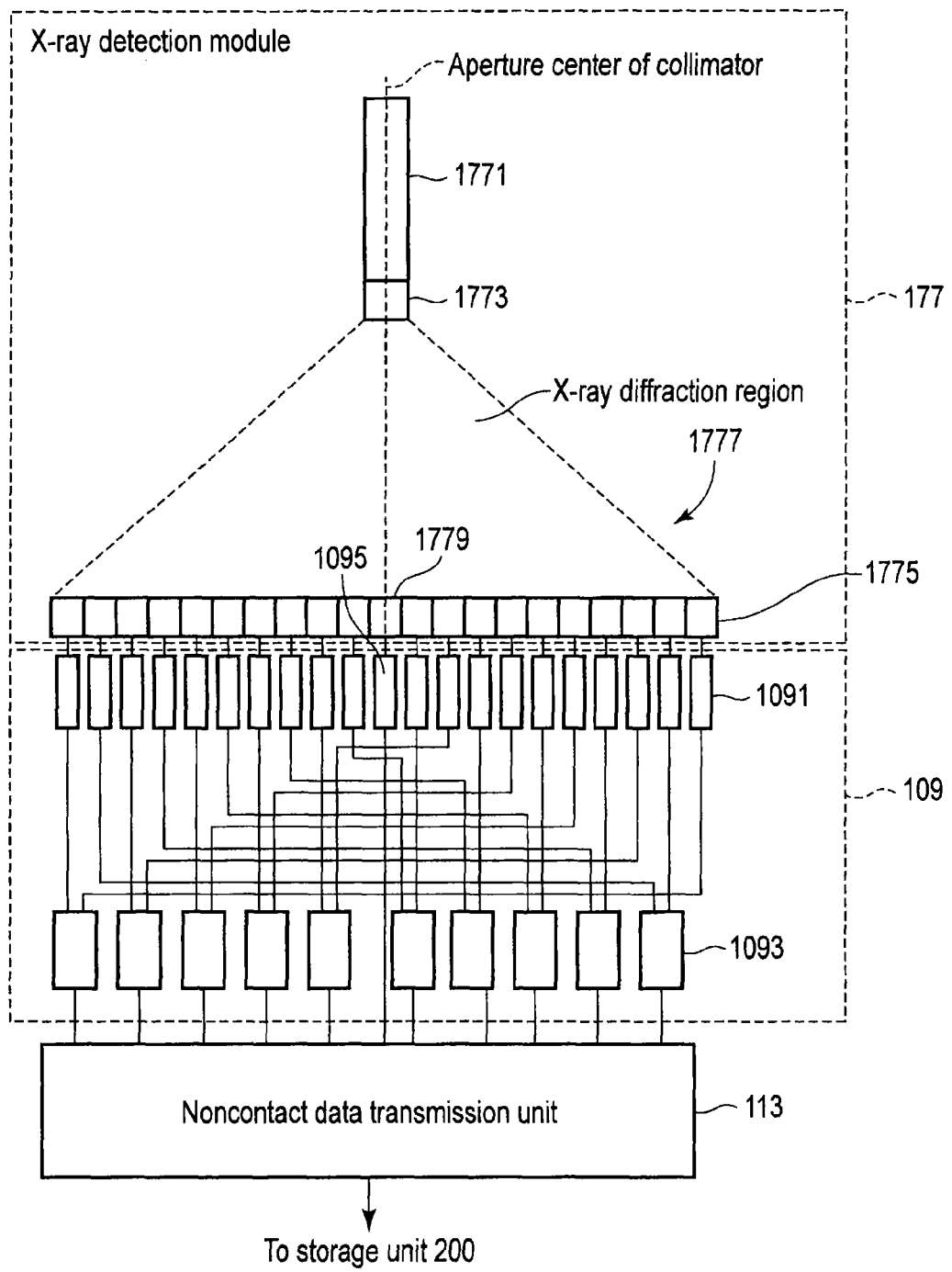
F I G. 4

X-RAY COMPUTED TOMOGRAPHY APPARATUS, X-RAY DETECTION APPARATUS, AND X-RAY DETECTION MODULE

CROSS-REFERENCE TO RELATED APPLICATIONS

This application is a Continuation application of PCT Application No. PCT/JP2013/079012, filed Oct. 25, 2013 and based upon and claims the benefit of priority from the Japanese Patent Application No. 2012-236555, filed Oct. 26, 2012, the entire contents of all of which are incorporated herein by reference.

FIELD

Embodiments described herein relate generally to an X-ray computed tomography apparatus including a counter, an X-ray detection apparatus capable of energy discrimination, and an X-ray detection module.

BACKGROUND

An attempt to put a photon counting type X-ray computed tomography apparatus (to be referred to as a photon counting X-ray CT apparatus hereinafter) into practice has been made in the form of expanding a technique for single photon detection (to be referred to as a single photon detection technique hereinafter) in nuclear medicine diagnostic apparatuses such as a single photon emission computed tomography apparatus (to be referred to as a SPECT apparatus hereinafter) and a positron emission computed tomography apparatus (to be referred to as a PET apparatus hereinafter). Single photon detection techniques are roughly categorized into two types.

The first type of single photon detection technique is as follows. First of all, a crystal (scintillator) or the like converts an X-ray photon transmitted through an object into scintillation light. A photodetector such as a photomultiplier tube (to be referred to as a PMT hereinafter) or silicon photomultiplier (to be referred to as an SiPM hereinafter) detects the scintillation light to extract an X-ray photon as an electrical signal. The above method is called an indirect conversion type method.

The second type of single photon detection technique is a method (also called a direct conversion type) which directly converts an X-ray photon transmitted through an object into an electrical signal by using a semiconductor detector. More specifically, a bias voltage is applied in advance to the two electrodes of the semiconductor detector. When an X-ray photon enters the semiconductor detector, the detector internally produces a pair of an electron and a hole. The generated electron and hole are respectively attracted to different electrodes. The electron which has reached the electrode is extracted as an electrical signal.

In either of the above methods, since the integral value of the intensity of the extracted electrical signal (to be referred to as a detection signal hereinafter) is proportional to the energy of the X-ray photon, detection signals are integrated. Integrating detection signals will calculate the energy of individually detected X-ray photon. The difference between the nuclear medicine diagnostic apparatus and the photon counting X-ray CT apparatus is that the flow rate of photons in the photon counting X-ray CT apparatus is much higher than that in the nuclear medicine diagnostic apparatus. In order to reconstruct a medical image by using the photon counting X-ray CT apparatus, it is necessary to perform, for example, single photon detection with respect to $10^9$ photons per $mm^2$ per sec (to be referred to as a count rate hereinafter).

When, however, executing single photon detection for X-ray photons with respect to the above count rate, the aforementioned two types of single photon detection techniques have the following two problems associated with count losses which respectively correspond to them. The problem in the first single photon detection technique is the problem of a count loss due to pileup. Pileup occurs within a typical attenuation time (several nsec) of scintillation when a plurality of X-ray photons enters the scintillator. Pileup is a phenomenon in which a plurality of detection signals respectively corresponding to a plurality of X-ray photons overlap. When pileup occurs, a plurality of X-ray photons are counted as one X-ray photon, resulting in the occurrence of a count loss.

The problem in the second single photon detection technique is the problem of a count loss due to the entrance of X-ray photons to the semiconductor detector during the dead time of the semiconductor detector. The dead time is the time interval from the instant a detection signal is extracted from the semiconductor detector to the instant the semiconductor detector becomes ready for pair production again. When an X-ray photon enters the semiconductor detector in the dead time, no pair production occurs, and hence no X-ray photon is counted. Currently, an attempt has been made to decrease the number of X-ray photons entering the same semiconductor detector in a unit time by lessening the size (pixel size) of the semiconductor detector. In this attempt, however, the maximum count rate has stayed around $10^6$ photons per $mm^2$ per sec.

The problem associated with the above count losses occurs because detection signals with long attenuation time constants are integrated to calculate the energy of an X-ray photon entering the X-ray detector.

SUMMARY OF INVENTION

Technical Problem

In order to implement a photon counting X-ray CT apparatus, it is a challenge to achieve a high count rate. It is, however, difficult to find the above single photon detection technique on the extension of the technique associated with a nuclear medicine diagnostic apparatus.

BRIEF DESCRIPTION OF THE DRAWINGS

FIG. 1 is a block diagram showing an example of the arrangement of an X-ray computed tomography apparatus according to an embodiment.

FIG. 3 is a view showing an example of an X-ray detection module in the X-ray detection circuit according to this embodiment, together with incident polychromatic X-rays and X-rays diffracted in accordance with energies.

FIG. 4 is a view showing an example of connecting a plurality of counters to a plurality of adders according to this embodiment.

DETAILED DESCRIPTION

Figure 2:
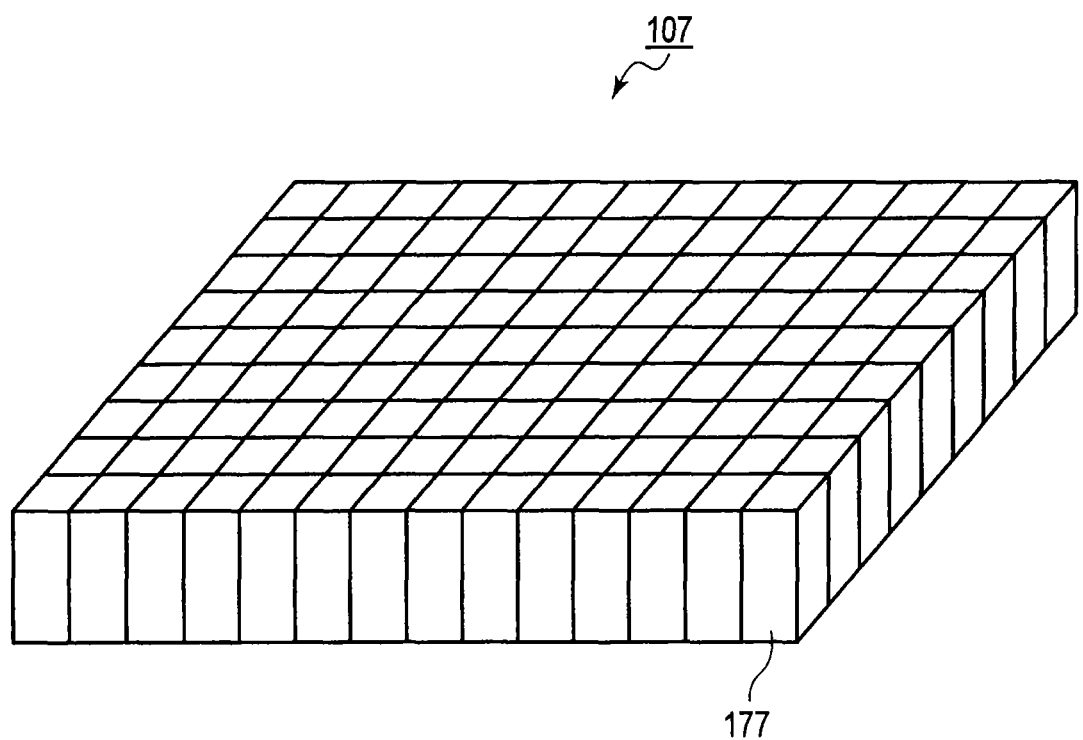
FIG. 2 is a perspective view showing an example of the array of a plurality of X-ray detection modules in an X-ray detection circuit according to this embodiment.

An X-ray computed tomography apparatus according to an embodiment includes an X-ray generation circuit, an X-ray detection circuit, a counting circuit, and a reconstruction circuit.

The X-ray generation circuit generates X-rays.

The X-ray detection circuit includes X-ray detection modules detecting X-rays generated by the X-ray generation circuit for respective energy widths.

The counting circuit counts a photon originating from the X-rays for the respective energy widths based on an output from the X-ray detection circuit.

The reconstruction circuit reconstructs a medical image based on an output from the counting circuit.

Each of the X-ray detection modules includes a collimator, a diffraction cell, and a plurality of X-ray detection cells.

The collimator collimates the X-rays.

The diffraction cell is arranged on a rear surface side of the collimator and configured to diffract the X-ray at an angle corresponding to an energy of the X-ray.

The X-ray detection cells are arranged at a predetermined distance away from a rear surface of the collimator, and detect the diffracted X-ray.

An embodiment of an X-ray computed tomography apparatus based on photon counting will be described with reference to the accompanying drawings. Note that there are various types of X-ray computed tomography apparatuses such as Rotate/Rotate-Type in which an X-ray generation circuit and X-ray detection circuit integrally rotate around an object, and Stationary/Rotate-Type in which many X-ray detection cells arrayed in a ring shape are fixed and only an X-ray generation circuit rotates around an object. Any type of X-ray computed tomography apparatus is applicable to the embodiment. Reconstruction of a medical image requires projection data for 360° corresponding to one rotation around an object. Even the half-scan method requires projection data for 180° +fan angle. Either reconstruction method is applicable to the embodiment. Recently, with advances toward the commercialization of a so-called multi-tube type X-ray computed tomography apparatus having a plurality of pairs of X-ray generation circuits and X-ray detection circuits mounted on a rotating ring, related techniques have been developed. The embodiment can be applied to both a conventional single-tube type X-ray computed tomography apparatus and a multi-tube type X-ray computed tomography apparatus. The single-tube type X-ray CT apparatus will be exemplified here. the energy widths based on a count value corresponding to each of the energy widths.

Note that the same reference numerals in the following description denote constituent elements having almost the same functions and arrangements, and a repetitive description will be made only when required.

FIG. 1 is a block diagram showing an example of the arrangement of an X-ray computed tomography apparatus based on photon counting according to this embodiment. An X-ray computed tomography apparatus 1 based on photon counting includes a gantry unit 100, a storage unit 200, a reconstruction circuit 300, a display unit 400, an input unit 500, and a control unit 600.

The gantry unit 100 houses a rotation support mechanism. The rotation support mechanism includes a rotating ring 101, a ring support mechanism which supports the rotating ring 101 to be freely rotatable about the rotation axis Z, and a rotation driving unit 103 (motor) which drives the ring to rotate. The rotating ring 101 is equipped with an X-ray generation circuit 105, an X-ray detection circuit 107, and a counting circuit 109 which counts the number of photons originating from X-rays based on an output from the X-ray detection circuit 107.

The X-ray generation circuit 105 includes a high voltage generator and an X-ray tube (neither of which is shown). The high voltage generator generates a high voltage (to be referred to as a tube voltage hereinafter) to be applied to the X-ray tube and a current (to be referred to as a tube current hereinafter) to be supplied to the X-ray tube. The high voltage generator generates a tube voltage and a tube current in accordance with the control signals input from the control unit 600 (to be described later) via a slip ring 111. The X-ray tube emits X-rays from an X-ray focus upon receiving a tube voltage and a tube current from the high voltage generator. The X-ray tube generates polychromatic X-rays. Polychromatic X-rays include monochromatic X-rays having different energies.

The X-ray detection circuit 107 includes a plurality of X-ray detection modules which detect X-rays for the respective energy widths. In the following description, assume that each of the plurality of X-ray detection modules corresponds to one channel. FIG. 2 is a view showing an example of the array of a plurality of X-ray detection modules 177 in the X-ray detection circuit 107. As shown in FIG. 2, the plurality of X-ray detection modules 177 are arranged in a matrix. Note that the plurality of X-ray detection modules 177 may be one-dimensionally arranged along the short-axis (Y-axis) direction of the top or the arc direction of the rotating ring 101. FIG. 3 is a view showing an example of the X-ray detection modules 177, together with polychromatic X-rays (to be referred to as incident X-rays hereinafter) entering a collimator 1771 and X-rays diffracted by a diffraction cell 1773 in accordance with the energies of X-rays.

The X-ray detection module 177 includes a collimator 1771, the diffraction cell 1773, and a plurality of X-ray detection cells 1775. The collimator 1771 collimates incident X-rays. The incident X-rays are polychromatic X-rays influenced by scattering, absorption, transmission, and the like corresponding to a substance in a transmission path of an object and the energies of monochromatic X-rays.

The diffraction cell 1773 is provided (arranged) on the rear surface side of the collimator 1771. The diffraction cell 1773 has a predetermined thickness. The diffraction cell 1773 is made of, for example, a metal or crystal powder. The diffraction cell 1773 diffracts the collimated polychromatic X-rays in accordance with energies. The polychromatic X-rays entering the diffraction cell 1773 are a group of polychromatic photons (i.e., a group of photons having a plurality of energies respectively corresponding to a plurality of wavelengths). For this reason, the diffraction cell 1773 diffracts a group of polychromatic photons at angles corresponding to energies of photons based on the Bragg condition. That is, the diffraction cell 1773 diffracts (performs spectroscopy) polychromatic X-rays at angles corresponding to energies. The plurality of X-ray detection cells 1775 (to be referred to as an X-ray detection cell group 1777 hereinafter) are provided (arranged) a predetermined distance away from the collimator 1771. The X-ray detection cell (to be referred to as the central cell hereinafter) located in the center of the X-ray detection cell group 1777 is provided at, for example, a position to face the aperture center of the collimator 1771. That is, the collimator 1771 is provided immediately above the central cell through the diffraction cell 1773. The width of the X-ray detection cell group 1777 is larger than the aperture of the collimator 1771. As shown in FIG. 3, each of the plurality of X-ray detection cells 1775 are two-dimensionally arranged on the matrix (to be referred to as a two-dimensional array hereinafter). Note that the plurality of X-ray detection cells 1775 may be one-dimensionally arranged. A counter 1091 (to be described later) is connected to each of the plurality of X-ray detection cells 1775. The space between the diffraction cell 1773 and the X-ray detection cell group 1777 is filled with a substance having a small refractive index such as air. Note that the space between the diffraction cell 1773 and the X-ray detection cell group 1777 may be vacuum.

More specifically, each of the X-ray detection cells 1775 is, for example, a pulse generation cell. That is, each of the plurality of X-ray detection cells generates a predetermined pulse signal upon reception of an X-ray diffracted by the diffraction cell 1773. The X-ray detection cells 1775 output the generated pulse signals to the counters 1091. The number of pulse signals corresponds to the number of X-ray photons (to be referred to as a photon count hereinafter) originating from monochromatic X-rays entering the X-ray detection cells 1775.

Assume that in FIG. 3, polychromatic X-rays include a first monochromatic X-ray having a first wavelength $\lambda 1$ and a second monochromatic X-ray having a second wavelength $\lambda 2$. Assume that the first wavelength $\lambda 1$ is shorter than the second wavelength $\lambda 2$. At this time, the Bragg angle with respect to the first monochromatic X-ray is smaller than that with respect to the second monochromatic X-ray. Owing to this, a plurality of different monochromatic X-rays included in the polychromatic X-rays which have entered the diffraction cell 1773 diffract at different angles corresponding to energies. If the X-ray detection cell group 1777 is a two-dimensional array, a plurality of different monochromatic X-rays reach a Debye-Scherrer ring corresponding to energies on the two-dimensional array.

The counting circuit 109 counts the pulse signals output from the plurality of X-ray detection cells 1775 of each of the plurality of X-ray detection modules 177. That is, the counting circuit 109 counts the photon number of X-ray photons entering the respective X-ray detection cells 1775.

FIG. 4 is a view concerning the X-ray detection modules 177 and the counting circuit 109 and showing an example of connecting the plurality of counters 1091 to a plurality of adders 1093. As shown in FIG. 4, the plurality of counters 1091 are respectively connected to the plurality of X-ray detection cells 1775. The adders 1093 are respectively connected to the plurality of counters 1091 respectively connected to the plurality of X-ray detection cells 1775 located in the same radius centered on a position (a central cell 1779) facing the aperture center of the collimator 1771. A counter 1095 connected to the central cell 1779 and the plurality of adders 1093 are connected to a noncontact data transmission unit 113. X-ray detection cells located nearer to the central cell 1779 have incident X-ray photons of higher energies, and X-ray detection cells located farther from the central cell 1779 have incident X-ray photons of lower energies. That is, for example, as shown in FIG. 3, the energy of the first monochromatic X-ray is higher than that of the second monochromatic X-ray.

More specifically, the counting circuit 109 includes the plurality of counters 1091 which count the photon and the plurality of adders 1093 which add the plurality of photon counts output from the plurality of counters 1091. Note that the counting circuit 109 may be provided inside or outside the gantry 100 via the noncontact data transmission unit 113 independently of the rotating ring 101. The data output from the counting circuit 109 is transmitted to the storage unit 200 via the noncontact data transmission unit 113 using magnetic transmission/reception or optical transmission/reception.

The plurality of counters 1091 are respectively connected to the plurality of X-ray detection cells 1775 and count the pulse signals output from the plurality of X-ray detection cells 1775. The plurality of counters 1091 are connected to the adders 1093 in accordance with the distances (radii) from the center of the X-ray detection cell group 1777. The plurality of adders 1093 are respectively connected to the plurality of counters 1091 in accordance with the distances from the central position of the X-ray detection cell group 1777. Note that the adder 1093 may not be connected to the central cell 1779. The adders 1093 add the plurality of count values output from the plurality of counters 1091. The adders 1093 output the added count value to the storage unit 200 via the noncontact data transmission unit 113.

The storage unit 200 stores the count value output via the noncontact data transmission unit 113. More specifically, the storage unit 200 stores count values in correspondence with a plurality of view angles, the plurality of X-ray detection modules 177, and a plurality of energy widths. Data concerning count values (frequencies) for the respective view angles, the respective X-ray detection modules 177 (channels), and the respective energy widths will be referred to as histogram data hereinafter. The storage unit 200 stores the count values output from the counting circuit 109 as histogram data.

The storage unit 200 stores the medical image reconstructed by the reconstruction circuit 300 (to be described later). The storage unit 200 stores information such as instructions, image processing conditions, and imaging conditions input by the operator with the input unit 500 (to be described later). The storage unit 200 stores control programs and the like which control the gantry 100 and the like for X-ray computed tomography.

Figure 5:
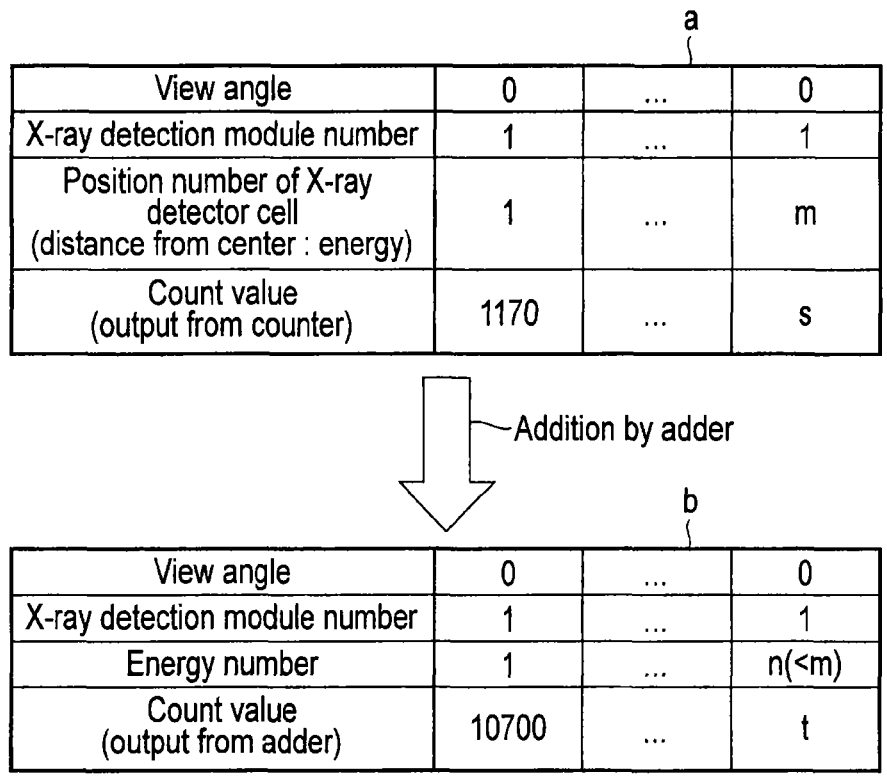
FIG. 5 is a view showing an example of a table corresponding to histogram data used for the reconstruction of a medical image according to this embodiment.

FIG. 5 is a view showing an example of a table corresponding to histogram data used for the reconstruction of a medical image. Outputs a from the counters in FIG. 5 indicate an example of a plurality of count values respectively corresponding to the position numbers (1 to m) of the X-ray detection cells 1775 when the view angle is 0° and the number of the X-ray detection module 177 (channel) is 1. A plurality of position numbers corresponding to the plurality of X-ray detection cells 1775 in a in FIG. 5 correspond to a plurality of different energy widths. That is, the positions of the plurality of X-ray detection cells 1775 correspond to the energies of X-ray photons corresponding to radii from the central cell 1779. The adders 1093 add count values with the same energy in correspondence with the outputs a in FIG. 5.

In FIG. 5, b represents an example of histogram data, of the plurality of count values in a in FIG. 5, which correspond to the results obtained by adding a plurality of count values respectively corresponding to a plurality of X-ray detection cells with the same radius from the central cell 1779. The polychromatic X-rays entering the collimator 1771 in each of the plurality of X-ray detection modules for each view angle are discriminated as a count value corresponding to energy. A preprocessing unit (not shown) or the like executes various types of correction for histogram data. Histogram data corresponds to, for example, projection data. A total number n of energy numbers of histogram data in b in FIG. 5 is smaller than a total number m of the position numbers of the X-ray detection cells.

The reconstruction circuit 300 reconstructs medical images corresponding to energy widths based on histogram data as count values respectively corresponding to a plurality of view angles, a plurality of X-ray detection modules, and a plurality of energy widths. For example, the reconstruction circuit 300 reconstructs medical images by a filter correction back projection method (e.g., a convolution back projection method) or a successive approximation method (e.g., an OS-EM method). Note that the reconstruction circuit 300 can reconstruct a plurality of medical images respectively corresponding to a plurality of energy widths, based on count values, for the respective view angles, the respective X-ray detection modules 177, and the respective energy widths.

Note that the reconstruction circuit 300 can also generate an energy difference image based on a plurality of medical images respectively corresponding to a plurality of energy widths. In addition, the reconstruction circuit 300 can reconstruct a medical image corresponding to an energy difference based on histogram data corresponding each of a plurality of energy widths.

The display unit 400 displays the medical image reconstructed by the reconstruction circuit 300 for each energy width, conditions set for X-ray computed tomography, and the like.

The input unit 500 inputs imaging conditions for X-ray computed tomography, which are desired by the operator, information about an object, and the like. More specifically, the input unit 500 inputs various instructions, commands, information, selections, and settings from the operator to the X-ray computed tomography apparatus 1. Although not shown, the input unit 500 includes a track ball for performing, e.g., setting of a region of interest, a switch button, a mouse, and a keyboard. The input unit 500 detects the coordinate point of a cursor displayed on the display screen, and outputs the detected coordinate point to the control unit 600. Note that the input unit 500 may be a touch panel arranged to cover the display screen. In this case, the input unit 500 detects a touched and indicated coordinate point based on a coordinate reading principle such as an electromagnetic induction method, electromagnetic distortion method, or pressure sensitive method, and outputs the detected coordinate point to the control unit 600.

The control unit 600 functions as the main unit of the photon counting X-ray computed tomography apparatus 1. The control unit 600 includes a CPU and a memory (neither of which is shown). The control unit 600 controls a bed unit (not shown), the gantry unit 100, the rotation driving unit 103, the X-ray generation circuit 105, and the like for X-ray computed tomography based on examination schedule data and control programs stored in the memory (not shown). More specifically, the control unit 600 temporarily stores, in a memory (not shown), information such as the instructions, image processing conditions, and the like input by the operator and sent from the input unit 500. The control unit 600 controls the bed unit, the gantry unit 100, the rotation driving unit 103, the X-ray generation circuit 105, and the like based on these pieces of information temporarily stored in the memory. The control unit 600 reads out control programs for executing predetermined image generation/display processing and the like from the storage unit 200, expands the programs in its own memory, and executes computation, processing, and the like associated with various types of processes.

(X-ray Photon Discrimination Function)

The X-ray photon discrimination function is a function of discriminating polychromatic X-rays entering the collimators 1771 of the respective X-ray detection modules 177 in accordance with energies. A process (to be referred to as an X-ray photon discrimination process hereinafter) associated with the X-ray photon discrimination function will be described below.

Figure 6:
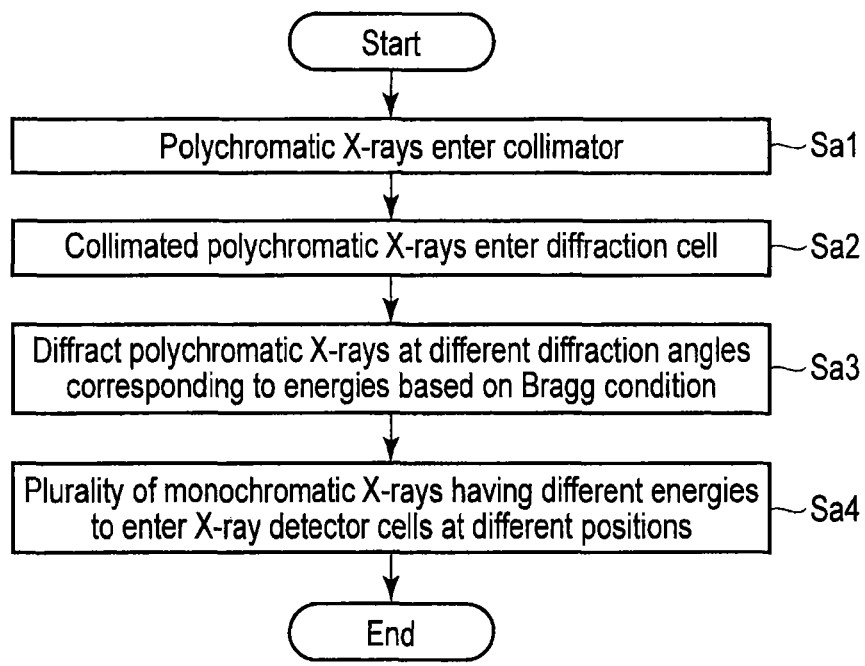
FIG. 6 is a flowchart concerning a process of performing energy discrimination of X-ray photons entering an X-ray detection cell according to this embodiment.

FIG. 6 is a flowchart showing an example of a procedure in an X-ray photon discrimination process.

Polychromatic X-rays enter the collimators 1771 of the plurality of X-ray detection modules 177 in the X-ray detection circuit 107 (step Sa1). The polychromatic X-rays collimated by the collimator 1771 enter the diffraction cell 1773 (step Sa2). The diffraction cell 1773 diffracts a plurality of X-ray photons of the polychromatic X-rays at different diffraction angles respectively corresponding to the energies of X-ray photons based on the Bragg condition (step Sa3). A plurality of monochromatic X-rays (X-ray photons) having different energies enter the X-ray detection cells 1775 at different positions (step Sa4). The positions of the X-ray detection cells 1775 correspond to the energies of the diffracted monochromatic X-rays.

(Energy Discrimination Reconstruction Function)

The energy discrimination reconstruction function is a function of reconstructing medical images for the respective energies based on count values (histogram data) concerning the positions of the X-ray detection cells 1775 corresponding to the respective energies. Processing concerning the energy discrimination reconstruction function (to be referred to as energy discrimination reconstruction processing hereinafter) will be described below.

Figure 7:
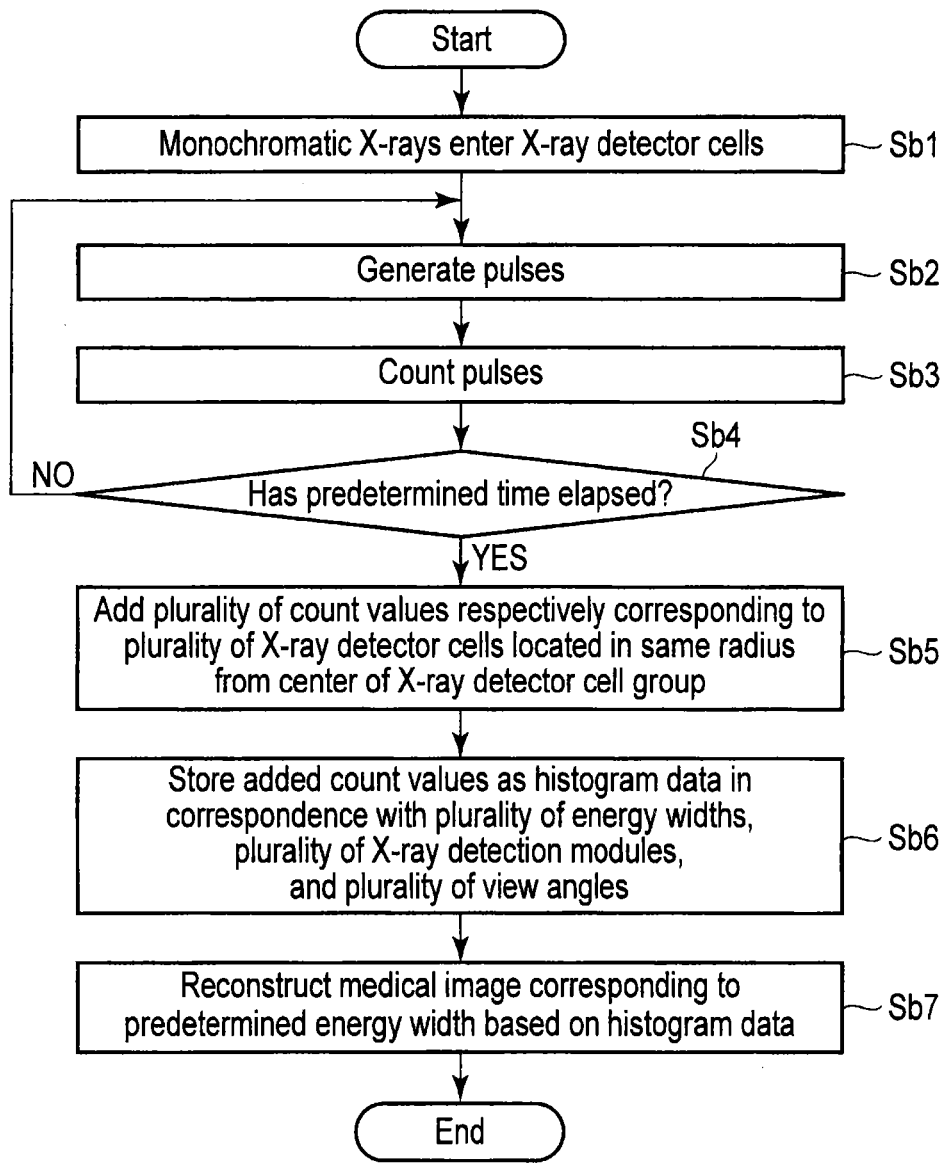
FIG. 7 is a flowchart showing a processing procedure for reconstructing a medical image corresponding to a predetermined energy width based on histogram data according to this embodiment.

FIG. 7 is a flowchart showing a processing procedure for reconstructing a medical image corresponding to a predetermined energy width based on histogram data.

A monochromatic X-ray enters the X-ray detection cell 1775 (step Sb1). The X-ray detection cell 1775 generates a pulse signal (step Sb2). The pulse count of the pulse signal is measured (step Sb3). The apparatus repeats processing in steps Sb2 and Sb3 until the elapse of a predetermined time (e.g., the time during which the X-ray detection circuit 107 is located at the same view angle) (step Sb4).

In the X-ray detection cell group 1777, a plurality of count values respectively corresponding to the plurality of X-ray detection cells 1775 located in the same radius are added (step Sb5). This determines the count values of X-ray photons discriminated for the respective energies concerning polychromatic X-rays entering the collimators 1771. The added count values are stored as histogram data in correspondence with a plurality of energy widths, a plurality of X-ray detection modules 177 (channels), and a plurality of view angles (step Sb6). The apparatus reconstructs medical images corresponding to the energy widths based on the histogram data for the respective energy widths (step Sb7).

According to the above arrangement, the following effect can be obtained.

The X-ray computed tomography apparatus 1 according to this embodiment can discriminate polychromatic X-rays entering the collimators 1771 into a plurality of monochromatic X-rays for the respective energy widths by an X-ray diffraction phenomenon corresponding to energies. According to this embodiment, since it is not necessary to integrate electrical signals to discriminate the energies of X-ray photons, it is possible to omit a process required for integrating electrical signals. According to the embodiment, this makes it possible to detect X-ray photons at a high count rate required by the photon counting X-ray CT apparatus.

In addition, this embodiment can simplify the circuit structure on the subsequent stage of the X-ray detection cells 1775. That is, according to the embodiment, the circuit structure includes the counters 1091 corresponding in number to the number of X-ray detection cells and a plurality of adders 1093 (half the number of columns of the X-ray detection cell group 1777 if the number of columns of the X-ray detection cell group 1777 is an even number or (number of columns−1)/2 if the number of columns of the X-ray detection cell group 1777 is an odd number). In addition, according to the embodiment, the X-ray detection cells 1775 are only required, to generate pulse signals upon reception of X-rays. For this reason, the signals output from the X-ray detection cells 1775 are not required to be quantitative. According to the embodiment, for example, simplifying the circuit can reduce the manufacturing cost.

According to the above description, this embodiment can provide a single photon detection technique by using an X-ray diffraction phenomenon which is not on the extension of a technique associated with a nuclear medicine diagnostic apparatus. In addition, simplifying the circuit can reduce the manufacturing cost of the photon counting X-ray CT apparatus 1.

Note that the X-ray detection circuit 107 in this embodiment can be implemented as an X-ray detection apparatus capable of energy discrimination. In this case, the X-ray detection apparatus has the structure shown in FIGS. 2 and 3. Furthermore, the X-ray detection module 177 in the embodiment can be implemented as a single X-ray detection module 177 capable of energy discrimination. In this case, the X-ray detection module 177 has the structure shown in FIG. 3. The X-ray photon discrimination function of a single X-ray detection apparatus or single X-ray detection module 177 complies with the flowchart shown in FIG. 6. As described above, according to the X-ray detection apparatus and the X-ray detection module 177, it is possible to provide a single photon detection technique by using an X-ray diffraction phenomenon which is not on the extension of a technique associated with a nuclear medicine diagnostic apparatus.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube configured to generate X-rays;
an X-ray detector including a plurality of X-ray detection modules configured to detect X-rays generated by the X-ray tube for respective energy widths;
a counting circuit configured to count photons originating from the X-rays for the respective energy widths based on an output from the X-ray detector; and
a reconstruction circuit configured to reconstruct a medical image based on an output from the counting circuit,
wherein each of the X-ray detection modules includes:
a collimator configured to collimate the X-rays;
a diffraction cell arranged on a rear surface side of the collimator and configured to diffract the X-ray at an angle corresponding to an energy of the X-ray; and
a plurality of X-ray detector cells arranged in a predetermined distance away from a rear surface of the collimator, and detecting the diffracted X-ray; and
wherein the counting circuit includes:
a plurality of counters respectively connected to the plurality of X-ray detector cells and configured to count the photons; and
an adder configured to add a plurality of count values outputted from the plurality of counters, which respectively correspond to the X-ray detector cells located in a same radius centered on a position facing an aperture center of the collimator in each of the X-ray detection modules.

2. The X-ray computed tomography apparatus of claim 1, wherein the diffraction cell is a crystal powder.

3. The X-ray computed tomography apparatus of claim 1, wherein the diffraction cell is a metal.

4. The X-ray computed tomography apparatus of claim 1, wherein a length of a column of the plurality of X-ray detector cells is longer than an aperture of the collimator.

5. The X-ray computed tomography apparatus of claim 1, wherein the reconstruction circuit is configured to reconstruct the medical image corresponding to each of the energy widths based on a count value corresponding to each of the energy widths.

* * * * *